(12) United States Patent
Imbert et al.

(10) Patent No.: US 7,846,926 B2
(45) Date of Patent: Dec. 7, 2010

(54) (POLY)AMINOACETAMIDE DERIVATIVES OF EPIPODOPHYLLOTOXIN THEIR PROCESS OF PREPARATION AND THEIR APPLICATIONS IN THERAPEUTICS AS ANTICANCER AGENTS

(75) Inventors: Thierry Imbert, Viviers-les-Montagnes (FR); Yves Guminski, Lagarrigue (FR); Jean-Marc Barret, Castres (FR); Anna Kruczynski, Pompertuzat (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 901 days.

(21) Appl. No.: 11/578,266

(22) PCT Filed: Apr. 14, 2005

(86) PCT No.: PCT/IB2005/001268

§ 371 (c)(1),
(2), (4) Date: Oct. 13, 2006

(87) PCT Pub. No.: WO2005/100363

PCT Pub. Date: Oct. 27, 2005

(65) Prior Publication Data

US 2009/0170843 A1 Jul. 2, 2009

(30) Foreign Application Priority Data

Apr. 16, 2004 (FR) .................................. 04 04053

(51) Int. Cl.
| | |
|---|---|
| *A61K 31/535* | (2006.01) |
| *A61K 31/497* | (2006.01) |
| *A61K 31/445* | (2006.01) |
| *A61K 31/335* | (2006.01) |
| *A01N 43/40* | (2006.01) |
| *A01N 43/26* | (2006.01) |
| *C07D 413/00* | (2006.01) |
| *C07D 405/00* | (2006.01) |
| *C07D 409/00* | (2006.01) |
| *C07D 211/22* | (2006.01) |
| *C07D 307/77* | (2006.01) |

(52) U.S. Cl. .............................. 514/232.8; 514/254.11; 514/321; 514/463; 544/148; 544/378; 546/197; 549/298

(58) Field of Classification Search .............. 514/232.8, 514/254.11, 321, 463; 544/148, 378; 546/197; 549/298
See application file for complete search history.

(56) References Cited

U.S. PATENT DOCUMENTS

| | | | |
|---|---|---|---|
| 5,332,811 A | 7/1994 | Lee et al. | |
| 6,008,382 A | 12/1999 | Imbert et al. | |
| 6,566,393 B1 | 5/2003 | Lee et al. | |
| 6,878,746 B2 | 4/2005 | Monneret et al. | |
| 7,087,641 B2 | 8/2006 | Kamal et al. | |

FOREIGN PATENT DOCUMENTS

| | | |
|---|---|---|
| EP | 0876374 A | 11/1998 |
| FR | 2742439 A1 | 6/1997 |
| FR | 2810321 A1 | 12/2001 |
| JP | 63-023884 A | 2/1988 |
| WO | WO-97/21713 A1 | 6/1997 |
| WO | WO-03/082876 A1 | 10/2003 |
| WO | WO-2004/000859 A2 | 12/2003 |
| WO | WO-2004-0733752 A2 | 9/2004 |

OTHER PUBLICATIONS

Zhang et al. Huaxue Xuebao, 2002 Abstract. vol. 60, Issue 4, pp. 720-724.*
Guianvarc'h, D., et al., "Synthesis and Biological Activity of Sulfonamide Derivatives of Epipodophyllotoxin", Journal of Medical Chemistry, American Chemical Society, 2004, vol. 47, pp. 2365-2374. XP-002514769.
Wang, Z. G., et al., "Synthesis and Antihumor Activities of 4-Acylamido-4-Deoxy-4'—Demethylepipodophyllotoxin Analogues", Shanghai Institute of Pharmaceutical Industry, Shanghai 200437, Acta Pharmacetica Sinica, 1993, vol. 28, No. 6, pp. 422-427.
Zhang, Fu-Min et al., Database Chemabs 'Online! Chemical Abstracts Service, Columbus, Ohio, US; 2002, XP002294249, retrieved from STN Database accession No. 2002:314033 abstract & Huaxue Xuebao, 60 (4), 720-724, Coden: HHHPA4; ISSN: 0567-7351, 2002.
Ma Weiyong: Chinese Journal of Medicinal Chemistry Zhongguo Yaowu Huaxue Zazhi, 5(3), 169-75, Coden: Zyhzef; ISSN: 1005-0108, vol. 5, No. 3, 1995.
Leeson et al. Drugs of the Future, vol. 21, No. 11, pp. 1136-1139, (1996).
Wang et al., Medicinal Research Reviews, vol. 17, No. 4, pp. 367-425 (1997).
Pagani et al., Cancer Chemother Pharmacol, vol. 38, No. 6, pp. 541-547, (1996). (Abstract only).
Mross et al., Cancer Chemother Pharmacol, vol. 38, No. 3, pp. 271-24 (1996). ) (Abstract only).
Xuebao et al., Acta Pharmacetical Sinica, vol. 28, No. 6, pp. 422-427, (1993).
Hansen et al., Acta Chem Scand, vol. 47, No. 12, pp. 1190-200, (1993). ) (Abstract only).
Thurston et al., J Med Chem, vol. 29, No. 8, pp. 1547-1550, (Aug. 1986). ). (Abstract only).
Phanstiel et al., J Org Chem, vol. 65, No. 18, pp. 5590-5599 (Sep. 8, 2000). (Abstract only).
Delcros et al., J Med Chem, vol. 45, No. 23, pp. 5098-5111, (Nov. 7, 2002) (Abstract only).

(Continued)

*Primary Examiner*—Sreeni Padmanabhan
*Assistant Examiner*—Samira Jean-Louis
(74) *Attorney, Agent, or Firm*—Birch, Stewart, Kolasch & Birch, LLP

(57) ABSTRACT

The present invention relates to novel podophyllotoxin derivatives substituted in the 4-position by a substituted (poly)aminoalkylaminoacetamide chain, to their process of preparation and to their use as medicament as anticancer agents.

8 Claims, No Drawings

OTHER PUBLICATIONS

Cohen et al., J. Chem. Soc., Chem. Commun., pp. 298-300, (1992).
Barret et al., Br J Cancer, vol. 83, No. 12, pp. 1740-1746, (Dec. 2000). (Abstract only).
Zhou et al., J Med Chem., vol. 34, No. 12, pp. 3346-3350, (Dec. 1991). (Abstract only).
Kruczynski et al., Cancer Chemother Pharmacol., vol. 41, No. 6, pp. 437-447, (1998). (Abstract only).
Imbert et al., "Synthesis and Biological Evaluation of New Cytotoxic Podophyllotoxin Derivatives Targeted for Polyamine Transporter", 2008 International Symposium on Medicinal Chemistry, Vienne, Pierre Fabre Medicament #P240.
Imbert et al., "Synthesis and SAR of a Series of Epipodophyllotoxin Polyarnine Conjugated Derivatives Vectorized for Active Polyamine Transporter System in Tumor Cells, Leading to the Selection of F14512 for Clinical Trials", 2009 AACR-NCI-EORTC Molecular Targets and Cancer Therapeutics, Pierre Fabre #A87.

* cited by examiner

(POLY)AMINOACETAMIDE DERIVATIVES OF EPIPODOPHYLLOTOXIN THEIR PROCESS OF PREPARATION AND THEIR APPLICATIONS IN THERAPEUTICS AS ANTICANCER AGENTS

The present invention relates to novel podophyllotoxin derivatives substituted in the 4-position by an optionally substituted (poly)aminoalkylaminoacetamide chain, to their process of preparation and to their use as medicaments, in particular as anticancer agents.

The compounds of the invention constitute derivatives of podophyllotoxin, a natural lignan known for its utility in the treatment of cancer. Other synthetic derivatives, such as etoposide and teniposide, are currently used as chemotherapeutic agents in the treatment in particular of small cell lung cancer. These various compounds act by inhibiting the catalytic activity of topoisomerase II.

The acetamide substitution in the β position on the podophyllotoxin backbone then represents a spermine or spermidine acetamide or more generally (poly)aminoalkylacetamide unit.

4'-Demethylepipodophyllotoxin derivatives are known as inhibitors of topoisomerase II. Their cytotoxic and antitumour activities have been demonstrated, in particular with etoposide, TOP 53 (*Drugs of the Future,* 1996, 21, 1136), GL 331 (*Medicinal Research Reviews,* 1997, 17, 367) and NK 611 (*Cancer Chemother. Pharmacol.,* 1996, 38, 217 and 541). Compounds having amino chains of benzylamine type directly bonded in the 4β-position of podophyllotoxin have been described (*J. Med. Chem.,* 1991, 34, 3346). Patent application FR 2 810 321 discloses podophyllotoxin carbamate or thiocarbamate derivatives of use in the treatment of cancer. Amide compounds in the 4β-position have also been disclosed (U.S. Pat. No. 6,566,393; *Acta Pharmacetica Sinica* (*Yaoxue Xuebao*), 1993, 28, 422; *Acta Chem. Scand.,* 1993, 47, 1190).

Patent EP 0 876 374 discloses a process for the demethylation of podophyllotoxin to obtain 4'-demethylepipodophyllotoxin, which is a synthetic intermediate in the preparation of etoposide and teniposide.

International Application WO 03/082876 discloses 4β-1''-[{2''-substituted benzoyl}aniline]podophyllotoxin analogues exhibiting an anticancer activity.

The need to have available more effective treatments encourages the search for novel molecules having different mechanisms of action which can then target types of tumours which are currently poorly treated or untreated and be free from problems of resistance. The availability of these novel products also makes it possible to prepare protocols with cotreatments which are more effective with regard to certain tumours.

The novel compounds of the present invention make it possible to respond to this problem.

The present invention relates to compounds of general formula (I)

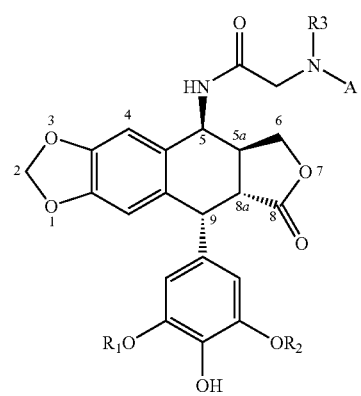

in which
R$_1$ and R$_2$ represent, independently of one another, a hydrogen atom or a methyl radical;
R3 and A together form a C$_3$-C$_8$ ring
or
R3 represents a radical chosen from the group consisting of a hydrogen atom, a C$_1$-C$_4$ alkyl radical and a benzyl radical and A represents a radical chosen from the group consisting of a hydrogen atom, a C$_1$-C$_4$ alkyl radical, a benzyl radical and a group of formula (II)

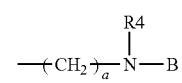

in which a varies from 2 to 5,
R4 and B together form a C$_3$-C$_8$ ring
or
R4 represents a radical chosen from the group consisting of a hydrogen atom, a C$_1$-C$_4$ alkyl radical and a benzyl radical, it being possible for R3 and R4 to be connected by an alkylene chain comprising 2 or 3 carbon atoms, and B represents a radical chosen from the group consisting of:
a hydrogen atom,
a C$_1$-C$_4$ alkyl radical,
a benzyl radical,
a group of formula (III)

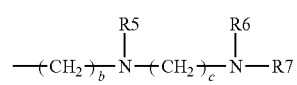

in which b and c can vary, independently of one another, from 2 to 5 and R5 to R7 represent, independently of one another, a radical chosen from the group consisting of a hydrogen atom, a C$_1$-C$_4$ alkyl radical and a benzyl radical, it being possible for R4 and R5 and/or R5 and R6 and/or R6 and R7 to be connected by an alkylene chain comprising 2 or 3 carbon atoms;

and a group of formula (IV)

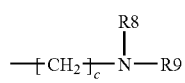

in which c can vary from 2 to 5 and R8 and R9 represent, each independently of one another, a hydrogen atom or a $C_1$-$C_5$ alkyl radical, it being possible for R4 and R8 to be connected by an alkylene chain comprising 2 or 3 carbon atoms, or R8 and R9 together form a $C_3$-$C_8$ ring;

or their pharmaceutically acceptable salts, in particular their addition salts, with inorganic or organic acids.

In the context of the present invention, the $C_3$-$C_8$ ling is advantageously an aliphatic ring which can comprise one or more heteroatoms, in particular oxygen.

According to an advantageous alternative form of the invention, in the formula (I), R3 to R9 represent, independently of one another, a hydrogen atom or a $C_1$-$C_4$ alkyl radical, advantageously a hydrogen atom or a methyl radical.

The compounds which are particularly advantageous in the context of the present invention are those in which R3 represents a hydrogen atom or a methyl radical and A represents a hydrogen atom, a methyl radical or a group of formula (II) in which R4 represents a hydrogen atom, a methyl radical or an ethyl radical and B represents a radical chosen from the group consisting of:
- a hydrogen atom,
- a methyl radical,
- an ethyl radical,
- a group of formula (III) in which R5, R6 and R7 represent a hydrogen atom, a $C_1$-$C_4$ alkyl radical or a benzyl radical,
- a group of formula (IV) in which R8 and R9, which are identical, represent a hydrogen atom or a methyl radical.

The preferred compounds according to the invention are chosen from the following compounds:
2-(2-dimethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-2-(2-(morpholin-4-yl)ethylamino)acetamide
2-[(2-dimethylaminoethyl)methylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-dimethylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-2-(piperidin-1-yl)acetamide
2-benzylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-2-(piperazin-1-yl)acetamide
2-(4-benzylpiperazin-1-yl)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-ethylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-2-(propylamino)acetamide
2-butylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-(2-diethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-(2-diethylaminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-amino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-(2-aminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-(3-aminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-(4-aminobutylamino)-N-[9-(4-hydroxy-3,5-dimethoxyphenyl)-9-oxo-5,5a,6,8,8a,9-hexahydrofuro[3',4':6,7]naphtho[2,3-d][1,3]dioxol-5-yl]acetamide
2-{(3-[4-(3-aminopropylamino)butylamino]propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-{3-[4-(3-aminopropylamino)butylamino]propylamino}-N-[9-(3,4-dihydroxy-5-methoxyphenyl)-8-oxo-5,5aS,6,8a,9-hexahydrofuro[3',4':6,7]naphtho[2,3-d][1,3]dioxol-5-yl]acetamide
2-{3-[4-(3-aminopropylamino)butylamino]propylamino}-N-[8-oxo-9-(3,4,5-trihydroxyphenyl)-5,5a,6,9,8a,9-hexahydrofuro[3',4':6,7]naphtho[2,3-d][1,3]dioxol-5-yl]acetamide
2-(4-aminobutylamino)-N-[9-(3,4-dihydroxy-5-methoxyphenyl)-8-oxo-5,5a,6,8,8a,9-hexahydrofuro[3',4':6,7]naphtho[2,3-d][1,3]dioxol-5-yl]acetamide
2-[3-(4-aminobutylamino)propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-[4-(3-aminopropylamino)butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-[3-(3-aminopropylamino)propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-[4-(4-aminobutylamino)butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-{3-[3-(3-aminopropylamino)propylamino]propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-{4-[4-(4-aminobutylamino)butylamino]butylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-{4-[4-(4-aminobutylamino)butylamino]butylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-[4-(4-aminobutylamino)butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide 2-(5-aminopentylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide and their addition salts with inorganic or organic acids.

More particularly the preferred compounds of the invention are chosen from the group consisting of:

2-[(2-dimethylaminoethylamino]-N-[9-(4-hydroxy-3,5-dimethoxyphenyl)-8-oxo-5,5,5a,6,8,8a,9-hexahydrofuro[3',4':6,7]naphtho[2,3-d][1,3]dioxol-5-yl]acetamide 2-dimethylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide 2-(4-aminobutylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide 2-{3-[4-(3-aminopropylamino)butylamino]propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide 2-[3-(4-aminobutylamino)propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide 2-[4-(3-aminopropylamino)butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide and their addition salts with inorganic or organic acids.

The isomers of the compounds according to the invention form an integral part of the invention.

Mention may be made, without implied limitation, among pharmaceutically acceptable acids, of hydrochloric, hydrobromic, sulphuric, phosphoric, acetic, trifluoroacetic, lactic, pyruvic, malonic, succinic, glutaric, fumaric, tartaric, maleic, citric, ascorbic, oxalic, methanesulphonic, camphoric and sulphamic acids.

The compounds according to the invention exhibit the characteristic of being soluble in water via the possibility of formation of inorganic or organic salts with the basic nitrogens of the side chain. This represents a very significant advantage in terms of administration, of formulation, of distribution, of pharmacokinetics and of bioavailability.

Another subject-matter of the present invention is the process for the preparation of the compounds according to the invention, which comprises the following successive stages:

a) starting from podophyllotoxin of formula (VIII)

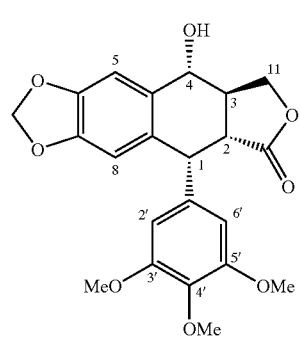

(VIII)

b) if appropriate, preparation by demethylation of a compound of formula (V)

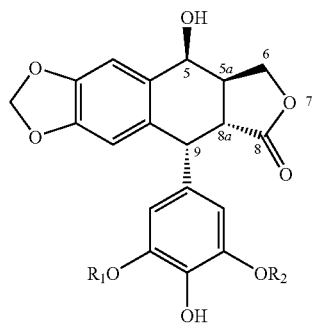

(V)

in which $R_1$ and $R_2$ are as defined in the compound of formula (I); then c) reaction of the compound of formula (V) or (VIII) with chloroacetonitrile in an acidic medium and then, if appropriate, demethylation reaction, to provide a compound of formula (VI)

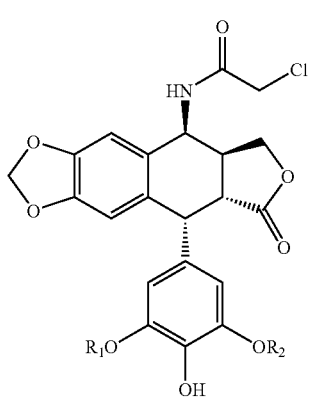

(VI)

in which $R_1$ and $R_2$ are as defined in the compound of formula (I); then d) reaction of the compound of formula (VI) with a compound of formula (VII)

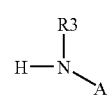

(VII)

in which R3 and A are as defined in the compound of formula (I), the amines optionally present in the group A being protected by an appropriate protective group advantageously chosen from the group consisting of a benzyl radical, a benzyloxycarbonyl (Z) radical or a tert-butyloxycarbonyl (Boc) radical, in a mixture of solvents comprising a polar aprotic solvent, in the presence of a Lewis base.

The atoms in podophyllotoxin, which is a natural product, are conventionally numbered according to a system different from that used in the context of the present invention for podophyllotoxin derivatives. Thus, in the context of the present invention, the compounds according to the invention (synthetic products) will be numbered according to the system given for the following compound of formula (I):

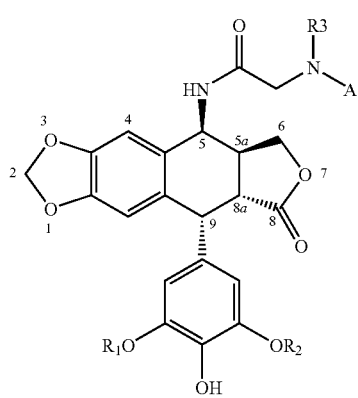

whereas podophyllotoxin is numbered according to the system conventionally used given above for the compound of formula (VIII).

According to an alternative form of the invention, a compound of formula (V), which is obtained by a demethylation reaction on podophyllotoxin, is prepared. Thus, 4'-demethyl-epipodophyllotoxin (Va) (the numbering used is that used for podophyllotoxin for formula (VIII)):

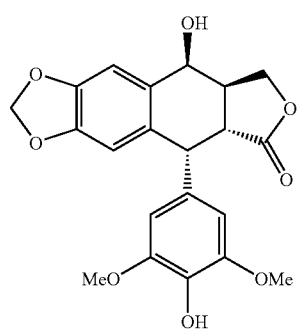

is obtained by a demethylation reaction on podophyllotoxin with the reagent pair methionine (or dimethyl sulphide)/methanesulphonic acid in the presence of trifluoroacetic acid or of acetone and of water, at a temperature of between $-10°$ C. and $40°$ C., according to the method disclosed in Patent FR 2 742 439.

It is also possible to obtain, with an excess of reagent and an additional reaction time, the didemethylation product, the compound of formula (V) in which $R_1$=H and $R_2$=Me (or $R_2$=H and $R_1$=Me) (Vb) (described in *J. Med. Chem.*, 1986, 29, 1547) and the tridemethylation product, the compound of formula (V) in which $R_1$=$R_2$=H (Vc), which is a novel product.

In stage c), the compound of formula (V) is subjected to a Ritter reaction with chloroacetonitrile in the presence of a strong acid, such as methanesulphonic acid or sulphuric acid, according to a process known to a person skilled in the art, analogously to the process described in the publication *Acta Chem. Scand.*, 1993, 47, 1190. This reaction results in the intermediates of formula (VI) in which $R_1$ and $R_2$ are as defined in the compound of formula (I).

During stage c), before the reaction of the compound of formula (V) with chloroacetonitrile, the mono-, di- and tri-demethylation compounds (formulae (Va), (Vb) and (Vc)) can be protected at their phenol functional groups with benzyloxycarbonyl groups, in order to prevent the synthesis of undesirable byproducts. These protective groups can subsequently be readily cleaved in a conventional way by hydrogenolysis in the presence of palladium-on-charcoal. However, the direct reaction of the compound of formula (V) with chloroacetonitrile can be carried out with the compounds of formulae (Va), (Vb) and (Vc) having unprotected phenol functional groups.

According to another alternative form of the invention, podophyllotoxin (VIII) is used directly as starting material.

The monodemethylation reaction is carried out subsequent to the Ritter reaction, during stage c), to result in the derivative of formula (VI) in which $R_1$=$R_2$=Me (VIa). Similarly, it is also possible to obtain, by an excess of reagent and an additional reaction time, the didemethylation product, the compound of formula (VI) in which $R_1$=H and $R_2$=Me (or $R_2$=H and $R_1$=Me) (VIb), and the tridemethylation product, the compound of formula (VI) in which $R_1$=$R_2$=H (VIc).

The reaction of stage d) is advantageously carried out at ambient temperature in a polar aprotic solvent, such as a mixture of acetonitrile and of DMF, in the presence of a base, such as triethylamine, and of potassium iodide. The potassium iodide makes it possible to substitute the chlorine present in the compound of formula (VI) by iodine, for better reactivity.

In the formula (VIII), mention may in particular be made, as examples of appropriate protective groups for the amine functional groups, of the tert-butyloxycarbonyl (BOC) and benzyloxycarbonyl (Z) groups. The protection of the amine functional groups makes it possible to avoid the synthesis of undesirable byproducts, in such a way that there is only a single site of reactivity during the coupling reaction.

The compounds of formula (VII) can be prepared according to the set of selective protections by protective groups for amines, for example BOC or Z, such as are indicated in Protective Groups in Organic Synthesis (Theodora W. Greene, 2nd Ed., John Wiley and Sons, 1991) or in *Synthesis*, 2002, 15, 2195; *Bull. Chem. Soc. Jpn.*, 1998, 71, 699; *Tet. Lett.*, 1998, 39, 439; *Tet. Lett.*, 2001, 42, 2709; *OPPI*, 1994, 26, 599; *Synthesis*, 1994, 37; *J. Org. Chem.*, 1998, 63, 9723; *Tet. Lett.*, 1994, 35, 2057 and 2061. These publications describe the preparation of the various amines with protective groups used. A person skilled in the art can proceed by analogy.

If appropriate, the final stage of the process according to the invention consists of the deprotection of the amine functional groups protected by appropriate groups.

The compounds of the present invention have chiral centres resulting from the natural origin of podophyllotoxin. In the compound of formula (V), the hydrogen atoms in the 5-, 5a-, 8a- and 9-positions have the following positions: H5α, H5aα, H8aβ, H9β. In the compound of formula (VI), the configuration of the asymmetric carbons is advantageously as follows: 5S, 5aS, 8aS, 9R.

The present invention also relates to the intermediate compound of formula (V) in which $R_1$, $R_2$ and $R_3$ represent a hydrogen atom.

Another subject-matter of the present invention is, as medicaments, the compounds of formula (I) according to the invention.

The compounds of the present invention exhibit an epipodophyllotoxin structure substituted in the 4-position by an acetamide group, itself optionally substituted by amines or polyamines.

Compounds having a polyamine chain grafted to a DNA-intercalating unit of acridine type (J. Org. Chem., 2000, 65, 5590; J. Med. Chem., 2002, 45, 5098) or an alkylating unit, such as chlorambucil (J. Chem. Soc. Chem. Commun., 1992, 298), have been described.

The compounds of the present invention, which are qualitatively and quantitatively different from the other known anticancer compounds, including etoposide, have the property of being agents which have the DNA as target and succeed in bringing about damage thereto.

The cell normally reacts, faced with damage to the DNA, by setting in motion repair systems which then ensure that it remains intact. With the compounds of the present invention, this repair process is not very effective and the cell then develops towards apoptosis. This phenomenon of cleavage of the DNA is displayed and measured by fluorescence in the comets test (vide infra).

The compounds of the present invention have in vitro cytotoxic properties and in vivo antitumour properties with regard to several murine models.

The compounds of the present invention exhibit an exceptional and surprising antitumour activity since they have the possibility of bringing about a significant and even complete regression of the tumour without causing side effects given solid form by loss in weight. This leads to the hope in the patient of effective activity with regard to non-solid tumours and solid tumours, such as melanomas, colorectal cancers, cancers of the lung, prostate, bladder, breast, uterus, stomach, pancreas or liver, ovarian cancers, leukaemias, in particular lymphomas and myelomas, ENT cancers and cancers of the brain.

A particular subject-matter of the present invention is a pharmaceutical composition, characterized in that it comprises at least one compound of formula (I) and an excipient appropriate for administration by the oral or parenteral route.

The pharmaceutical compositions according to the invention, which comprise at least one compound of formula (I) and an excipient appropriate for oral or parenteral administration, can be administered alone or in combination with other anticancer agents. They can be presented in a way suited for such administrations one or more times daily, in the injectable form, or in the form of capsules, including hard gelatin capsules, or tablets, at the dosage of 0.5 to 300 mg/m$^2$, by the injectable route, and of 1 to 100 mg/m$^2$, by the oral route.

Finally, the present invention relates to the use of a compound of formula (I) according to the invention in the preparation of a medicament intended for the anticancer treatment of non-solid tumours and solid tumours, such as melanomas, colorectal cancers, cancers of the lung, prostate, bladder, breast, uterus, stomach, pancreas or liver, ovarian cancers, leukaemias, in particular lymphomas and myelomas, ENT cancers and cancers of the brain.

According to an advantageous alternative form of the invention, the medicament comprises:
  a) the compound of formula (I) and
  b) an anticancer agent, as combination products for a use which is simultaneous, separate or spread out over time in the treatment of cancers and/or tumours.

In particular, the anticancer agent is chosen from the group consisting of platinum derivatives, taxanes, vincas and 5-FU.

In the context of the present invention, the medicament is also intended for the treatment of tumours which are resistant to conventional therapies.

The following examples male it possible to illustrate the invention and are not limiting. In the proton NMR spectra of the following examples, the numbering used for the assigning of the protons is that in use and shown on the structure of podophyllotoxin of formula (VIII). In contrast, the numbering used for the designation of the products synthesized is that used and defined for the compound of formula (I).

EXAMPLE 1

Preparation of the Compounds 5-(3,4-Dihydroxy-5-methoxyphenyl)-9-hydroxy-5,8,8a, 9-tetrahydro-5aH-furo[3',4':6,7]naphtho[2,3-d][1,3]dioxol-6-one; and 9-Hydroxy-5-(3,4,5-trihydroxyphenyl)-5,8,8a,9-tetrahydro-5aH-furo[3',4':6,7]naphtho[2,3-d][1,3]dioxol-6-one 10 g (24 mmol) of podophyllotoxin are dissolved in 60 ml of trifluoroacetic acid. 5.4 ml (72 mmol) of dimethyl sulphide and 47 ml (72 mmol) of methanesulphonic acid are successively added. Stirring is maintained for 9 hours, 5.4 ml (72 mmol) of dimethyl sulphide are again added and stirring is maintained for 9 hours. The medium is run quickly onto ice (600 ml) and extracted with ethyl acetate (3×300 ml). The organic phases are washed with water and then with a NaHCO$_3$ solution to neutrality. After drying over sodium sulphate, filtering and evaporating, 6.3 g of crude demethylation product are obtained. Flash chromatography on silica (elution: CH$_2$Cl$_2$/acetone 9/1) makes it possible to isolate 550 mg of 5-(4-hydroxy-3,5-dimethoxyphenyl)-9-hydroxy-5,8, 8a,9-tetrahydro-5aH-furo[3',4':6,7]naphtho[2,3-d][1,3]dioxol-6-one, that is to say 4'-demethylepipodophyllotoxin of formula (Va). 1.10·g of 5-(3,4-dihydroxy-5-methoxyphenyl)-9-hydroxy-5,8,8a,9-tetrahydro-5aH-furo[3',4':6,7]naphtho [2,3-d][1,3]dioxol-6-one (Analysed: C$_{20}$H$_{18}$O$_8$.0.15H$_2$O; calculated: C %, 61.74; H %, 4.74. found: C %, 61.67; H %, 4.68), and then 1.9 g of 9-hydroxy-5-(3,4,5-trihydroxyphenyl)-5,8,8a,9-tetrahydro-5aH-furo[3',4':6,7]naphtho[2,3-d] [1,3]dioxol-6-one are also isolated. The latter compound has a proton NMR spectrum with the following characteristics: $^1$H NMR (d$_6$-DMSO) δ 8.65 (m, 2H), 7.95 (m, 1H), 6.71 (s, 1H, H$_5$), 6.47 (s, 1H, H$_8$), 5.98 (d, 2H, J=2 Hz, OCH$_2$O), 5.93 (s, 2H, H$_{2'}$, H$_{6'}$), 4.68 (d, 1H, J=3.2 Hz, H$_4$), 4.34 (t, 1H, J=8 Hz, H$_{11a}$), 4.29 (d, 1H, J=5.2 Hz, H$_1$), 4.16 (dd, 1H, J=8 Hz, J'=10 Hz, H$_{11b}$), 3.17 (dd, 1H, J=5.2 Hz and J'=14 Hz, H$_2$), 2.76 (m, 1H, H$_3$).

EXAMPLE 2

Preparation of Carbonic Acid Benzyl Ester 2-benzyloxycarbonyloxy-5-(9-hydroxy-6-oxo-5,5a,6,8,8a,9-hexahydrofuro[3',4':6,7]naphtho[2,3-d][1,3]dioxol-5-yl)-3-methoxyphenyl Ester 2.65 ml (18.5 mmol) of benzyl chloroformate are introduced, at 0° C. under nitrogen, with stirring, into a solution of 2.4 g (6.2 mmol) of 5-(3,4-dihydroxy-5-methoxyphenyl)-9-hydroxy-5,8,8a,9-tetrahydro-5aH-furo[3',4':6,7]naphtho[2, 3-d][1,3]dioxol-6-one, obtained according to Example 1, in a 1/1 mixture of CH$_2$Cl$_2$ and THF in the presence of 4.3 ml (30 mmol) of triethylamine. The reaction is continued for 1 hour, then the medium is poured onto water and the organic phases are separated by settling, dried over sodium sulphate and evaporated. The dicarbonate compound obtained is crystallized from isopropyl ether (3.1 g, yield 76%). TLC SiO$_2$ (CH$_2$Cl$_2$/MeOH 95/5) Rf=0.6; $^1$H NMR (d$_6$-DMSO) δ 7.36 (m, 10H, Ar), 5.22 (s, 2H, benzyl CH$_2$), 5.17 (s, 2H, benzyl CH$_2$).

EXAMPLE 3

Preparation of Carbonic Acid Benzyl Ester 2,3-bis (benzyloxycarbonyloxy)-5-(9-hydroxy-6-oxo-5,5a,6,8,8a,9-hexahydrofuro[3',4':6,7]naphtho[2,3-d][1,3]dioxol-5-yl)phenyl Ester By the same reaction as in Example 2 but using 5-(3,4,5-trihydroxyphenyl)-9-hydroxy-5,8,8a,9-tetrahydro-5aH-furo[3',4':6,7]naphtho[2,3-d][1,3]dioxol-6-one instead of 5-(3,4-dihydroxy-5-methoxyphenyl)-9-hydroxy-5,8,8a,9-tetrahydro-5aH-furo[3',4':6,7]naphtho[2,3-d][1,3]dioxol-6-one, the tricarbonate derivative is obtained with a yield of 96%. TLC SiO$_2$ (CH$_2$Cl$_2$/MeOH 95/5) Rf=0.5; $^1$H NMR (d$_6$-DMSO) δ 7.38 (m, 10H, Ar), 7.31 (m, 5H, Ar), 5.21 (s, 4H, benzyl CH$_2$), 5.17 (s, 2H, benzyl CH$_2$).

EXAMPLE 4

Preparation of 2-chloro-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound can be obtained in two different ways.
a) 30 g of 4'-demethylepipodophyllotoxin of formula (Va) are added to 47.4 ml of chloroacetonitrile and then, with stirring, 3 drops of concentrated sulphuric acid are added. Stirring is maintained at ambient temperature for 3 hours. 300 ml of isopropanol are then added with stirring. The precipitate obtained is filtered off and washed with 200 ml of isopropanol. The precipitate is rinsed with water to neutral pH and then with ethyl ether. After drying under vacuum, 34.2 g (yield 96%) of a white solid are obtained. Melting point: 240° C.; $^1$H NMR (d$_6$-DMSO) δ 8.65 (d, 1H, J=7 Hz, NH), 8.26 (s, 1H, 4'-OH), 6.78 (s, 1H, H$_5$), 6.54 (s, 1H, H$_8$), 6.24 (s, 2H, H$_{2'}$, H$_{6'}$), 5.99 (d, 2H, J=11.3 Hz, OCH$_2$O), 5.17 (dd, 1H, J=4.56 and 7 Hz, H$_4$), 4.51 (d, 1H, J=5.2 Hz, H$_1$), 4.29 (t, 1H, J=8 Hz, H$_{11a}$), 4.10 (s, 2H, CH$_2$Cl), 3.78 (dd, 1H, J=8 Hz and 10 Hz, H$_{11b}$), 3.63 (s, 6H, 2×OCH$_3$), 3.15 (dd, 1H, J=5.2 and 14 Hz, H$_2$), 3.97 (m, 1H, H$_3$).
b) 0.2 ml of concentrated sulphuric acid is added at ambient temperature to 1 g of podophyllotoxin stirred in suspension in 2 ml of chloroacetonitrile. The solution becomes homogeneous. Stirring is maintained at ambient temperature for 2 h and then the reaction medium is poured onto ice and extracted with ethyl acetate. After separating by settling, drying over sodium sulphate and filtering, 840 mg of light brown crystals are obtained, corresponding to 2-chloro-N-[9-(3,4,5-trimethoxyphenyl)-8-oxo-5,5a,6,8,8a,9-hexahydrofuro[3',4':6,7]naphtho[2,3-d][1,3]dioxol-5-yl]acetamide. Melting point=145° C. TLC SiO$_2$ (CH$_2$Cl$_2$/MeOH 95/5, Rf=0.5); $^1$H NMR (d$_6$-DMSO) δ 4.1 (s, 2H, CH$_2$Cl).

This compound is demethylated according to the conditions of Example 1 to provide the same compound as above in Example 4a), with a yield of 20% after conventional chromatography.

EXAMPLE 5

Preparation of 2-chloro-N-[9-(3,4-dihydroxy-5-methoxyphenyl)-8-oxo-5,5a,6,8,8a,9-hexahydrofuro[3',4':6,7]naphtho[2,3-d][1,3]dioxol-5-yl]acetamide According to the same procedure as in Example 4a) but with 5-(3,4-dihydroxy-5-methoxyphenyl)-9-hydroxy-5,8,8a,9-tetrahydro-5aH-furo[3',4':6,7]naphtho[2,3-d][1,3]dioxol-6-one obtained according to Example 1, a beige solid is isolated after flash chromatography on SiO$_2$ (elution: CH$_2$Cl$_2$/MeOH 98/2) with a yield of 28%. MS-ESI (m/z): 462.1 (MH+), 479.1 (MNH$_4$+).

EXAMPLE 6

Preparation of Carbonic Acid Benzyl Ester 2-benzyloxycarbonyloxy-5-[9-(2-chloroacetylamino)-6-oxo-5,5a,6,8,8a,9-hexahydrofuro[3',4':6,7]naphtho[2,3-d][1,3]dioxol-5-yl]-3-methoxyphenyl Ester According to the same procedure as in Example 4a) but using carbonic acid benzyl ester 2-benzyloxycarbonyloxy-5-(9-hydroxy-6-oxo-5,5a,6,8,8a,9-hexahydrofuro-[3',4':6,7]naphtho[2,3-d][1,3]dioxol-5-yl)-3-methoxyphenyl ester obtained in Example 2, carbonic acid benzyl ester 2-benzyloxycarbonyloxy-5-[9-(2-chloroacetylamino)-6-oxo-5,5a,6,8,8a,9-hexahydrofuro[3',4':6,7]naphtho[2,3-d][1,3]dioxol-5-yl]-3-methoxyphenyl ester is isolated with a yield of 83% in the form of a white foam. TLC SiO$_2$ (CH$_2$Cl$_2$/MeOH 95/5, Rf=0.63); $^1$H NMR (d$_6$-DMSO) δ 4.11 (s, 2H, CH$_2$Cl).

EXAMPLE 7

Preparation of 2-chloro-N-[8-oxo-9-(3,4,5-trihydroxyphenyl)-5,5a,6,8,8a,9-hexahydrofuro[3',4':6,7]naphtho[2,3-d][1,3]dioxol-5-yl]acetamide According to the same procedure as in Example 4a) but with 5-(3,4,5-trihydroxyphenyl)-9-hydroxy-5,8,8a,9-tetrahydro-5aH-furo[3',4':6,7]naphtho[2,3-d][1,3]dioxol-6-one obtained in Example 1, a beige foam is isolated after flash chromatography on SiO$_2$ (elution: CH$_2$Cl$_2$/MeOH 95/5) with a yield of 20%. MS-ESI (m/z): 448.0 (MH+), 465.0 (MNH$_4$+).

EXAMPLE 8

Preparation of Carbonic Acid Benzyl Ester 2,3-bis (benzyloxycarbonyloxy)-5-[9-(2-chloroacetylamino)-6-oxo-5,5a,6,8,8a,9-hexahydrofuro[3',4':6,7]naphtho[2,3-d][1,3]dioxol-5-yl]phenyl Ester According to the same procedure as in Example 4a) but using carbonic acid benzyl ester 2,3-bis(benzyloxycarbonyloxy)-5-(9-hydroxy-6-oxo-5,5a,6,8,8a,9-hexahydrofuro[3',4':6,7]naphtho[2,3-d][1,3]dioxol-5-yl)phenyl ester obtained in Example 3, carbonic acid benzyl ester 2,3-bis(benzyloxycarbonyloxy)-5-[9-(2-chloroacetylamino)-6-oxo-5,5a,6,8,8a,9-hexahydrofuro[3',4':6,7]naphtho[2,3-d][1,3]dioxol-5-yl]phenyl ester is isolated.

Preparation of the Final Compounds

EXAMPLE 9

Preparation of 2-(2-dimethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide 0.75 ml (5.2 mmol) of triethylamine and then a spatula tip of potassium iodide 10 are added to 1 g (2.1 mmol) of the compound of Example 4 in solution in 30 ml of acetonitrile and 3 ml of DMF. A solution of 0.6 ml (5.2 mmol) of N,N-dimethyl-1,2-ethanediamine in 10 ml of acetonitrile is then added with stirring at ambient temperature. Stirring is maintained for 2 days, then the reaction medium is evaporated and the residue is taken up with water (100 ml) and extracted with $CH_2Cl_2$ (3 times 25 ml); after separating by settling, the organic phase is dried over sodium sulphate, filtered and evaporated. The residue is purified by flash chromatography on Chromagel 60 AC silica (35-70 mesh) (eluent: $CH_2Cl_2$/MeOH/$NH_4OH$ 90/9/1). 400 mg of a white foam are obtained (yield 36%). The dihydrochloride is precipitated from acetone by addition of an isopropanol solution saturated with hydrochloric acid. Melting point=230° C.; $^1H$ NMR base ($d_6$-DMSO) δ 8.26 (m, 1H, OH), 8.20 (d, 1H, J=8.3 Hz, NH amide), 6.76 (s, 1H, $H_5$), 6.53 (s, 1H, $H_8$), 6.24 (s, 2H, $H_{2'-6'}$), 5.99 (d, J=11.56 Hz, $OCH_2O$), 5.20 (dd, 1H, J=8.3 and 4.7 Hz, $H_4$), 4.50 (d, 1H, J=5.2 Hz, $H_1$), 4.28 (t, 1H, J=8 Hz, $H_{11a}$), 3.73 (dd, 1H, J=10.8 and 8 Hz, $H_{11b}$), 3.63 (s, 6H, 2×OMe), 3.37 (m, 1H, NH), 3.19 (s, 2H, $CH_2CO$), 2.94 (m, 1H, H1), 2.50 (m, 4H, 2×$CH_2$), 2.08 (s, 6H, 2×$CH_3$); MS-ESI (m/z): 528.2' (MH+).

The following compounds are obtained by the same reaction but with the corresponding starting materials:

EXAMPLE 10

Preparation of N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-2-(2-morpholin-4-yl)ethylamino)acetamide This compound is prepared from the compound of Example 4 and 2-(morpholin-4-yl)ethanamine.
Dihydrochloride: Melting point=212° C.; MS-ESI (m/z): 570.2 (MH+).

EXAMPLE 11

Preparation of 2-[(2-dimethylaminoethyl)methylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is prepared from the compound of Example 4 and N,N,N-trimethyl-1,2-ethanediamide.
Dihydrochloride: M.p.=238° C.

EXAMPLE 12

Preparation of 2-dimethylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is prepared from the compound of Example 4 and dimethylamine.
Hydrochloride: M.p. (° C.)>260° C.; Analysed: $C_{25}H_{28}N_2O_8$.HCl; calculated: C %, 57.64; H %, 5.61; N %, 5.38. found: C %, 57.47; H %, 5.47; N %, 5.26.

EXAMPLE 13

Preparation of N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-2-(piperidin-1-yl)acetamide This compound is prepared from the compound of Example 4 and piperidine.
Hydrochloride: Melting point=269-270° C.; analysed: $C_{28}H_{32}N_2O_8$.HCl; calculated: C %, 59.95; H %, 5.93; N %, 4.99. found: C %, 59.57; H %, 6.25; N %, 4.96.

EXAMPLE 14

Preparation of 2-benzylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is prepared from the compound of Example 4 and benzylamine.
Hydrochloride: Melting point=225° C.

EXAMPLE 15

Preparation of N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-2-(piperazin-1-yl)acetamide This compound is prepared from the compound of Example 4 and piperazine.
Dihydrochloride: Melting point=237-8° C.

EXAMPLE 16

Preparation of 2-(4-benzylpiperazin-1-yl)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is prepared from the compound of Example 4 and N-benzylpiperazine.
Dihydrochloride: Melting point=205° C.

EXAMPLE 17

Preparation of 2-ethylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is prepared from the compound of Example 4 and ethylamine.

EXAMPLE 18

Preparation of N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-2-(propylamino)acetamide This compound is prepared from the compound of Example 4 and propylamine.

EXAMPLE 19

Preparation of 2-butylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is prepared from the compound of Example 4 and butylamine.

EXAMPLE 20

Preparation of 2-(2-diethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is prepared from the compound of Example 4 and N,N-diethyl-1,2-ethanediamine.

EXAMPLE 21

Preparation of 2-(2-diethylaminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is prepared from the compound of Example 4 and N,N-diethyl-1,3-propanediamine.

EXAMPLE 22

Preparation of 2-amino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is obtained in 2 stages from the compound obtained in Example 4. In a 1st stage, the compound of Example 4 is treated according to the process of Example 9, with benzylamine instead of N,N-dimethyl-1,2-ethanediamine. The corresponding benzylamino intermediate, that is to say the compound of Example 14 is obtained (TLC $SiO_2$ $CH_2Cl_2$/MeOH 95/5: Rf=0.34). In a 2nd stage, this intermediate is debenzylated: 830 mg of this intermediate are placed with vigorous stirring in a mixture of MeOH (30 ml) and THF (20 ml) with 100 mg of 10% palladium-on-charcoal and a hydrogen atmosphere for 8 h. The catalyst is subsequently filtered off and the filtrate is evaporated. Elution on a silica column ($CH_2Cl_2$/MeOH/$NH_4OH$-90/9/1) provides 300 mg of the debenzylated compound crystallized from AcOEt (yd 43%). The hydrochloride is formed in acetone by addition of isopropanolic HCl solution. Melting point=236° C.; MS-APCI (m/z) 457.1 (MH+).

EXAMPLE 23

Preparation of 2-(2-aminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is obtained in 2 stages from the compound obtained in Example 4. In a 1st stage, the compound of Example 4 is treated according to the process of Example 9, with benzyl 2-aminoethylcarbamate (*Synthesis*, 2002, 15, 2195, *Bull. Chem. Soc. Jpn.*, 1998, 71, 699) instead of N,N-dimethyl-1,2-ethanediamine. The intermediate having an N-benzyloxycarbonyl protective group is obtained, the hydrochloride of which is formed in acetone in the presence of isopropanol HCl solution. Melting point=178° C. MS-APCI (m/z) 634.3 (MH+). In a 2nd stage, this intermediate is treated, as in Example 22, with palladium-on-charcoal and hydrogen. The dihydrochloride is obtained with a yield of 89%. Melting point=236° C. Analysed: $C_{25}H_{29}N_3O_8$.2HCl; calculated: C %, 52.46; H %, 5.46; N %, 7.34. found: C %, 52.78; H %, 5.46; N %, 7.14.

EXAMPLE 24

Preparation of 2-(3-aminopropylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide The intermediate possessing an N-benzyloxycarbonyl protective group is obtained by the same reaction sequence as for Example 22 but using the corresponding starting materials; the hydrochloride of the intermediate is formed in acetone and ethyl ether in the presence of isopropanol HCl solution. Melting point=132° C. MS-APCI (m/z) 648.1 (MH+). Debenzylation according to the same process as in Example 22 provides the dihydrochloride. Melting point=219° C. MS-APCI (m/z) 514.3 (MH+).

EXAMPLE 25

Preparation of 2-(4-aminobutylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide The intermediate possessing an N-benzyloxycarbonyl protective group is obtained but the same reaction sequence as in Example 22 but using benzyl 4-aminobutylcarbamate, obtained according to *Tet. Lett.*, 2001, 42, 2709; the intermediate crystallizes in the base state from ethyl ether. Melting point=95-96° C. MS-APCI (m/z) 662.4 (MH+). Debenzylation subsequently provides the dihydrochloride. Melting point=201° C. MS-ESI (m/z) 528.2 (MH+). The hydrated form is formed with $3H_2O$. Melting point=223° C. Analysed: $C_{27}H_{33}N_3O_8$.2HCl; calculated: C %, 54.01; H %, 5.87; N %, 7.00. found C %, 53.64; H %, 5.63; N %, 6.85.

EXAMPLE 26

Preparation of 2-{3-[4-(3-aminopropylamino)-butylamino]propylamino}-N-[8-oxo-9-(3,4,5-trimethoxyphenyl)-5,5a,6,8,8a,9-hexahydrofuro[3',4':6,7]naphtho[2,3-d][1,3]dioxol-5-yl]acetamide This compound is obtained by the same procedure as in Example 22 but with the intermediate 2-chloro-N-[9-(3,4,5-trimethoxyphenyl)-8-oxo-5,5a,6,8,8a,9-hexahydrofuro[3',4':6,7]naphtho[2,3-d][1,3]dioxol-5-yl]acetamide obtained in Example 4b) and with benzyl{4-[(3-aminopropyl)benzyloxycarbonylamino]butyl}(3-benzyloxycarbonylaminopropyl)carbamate (*Tet. Lett.*, 1998, 39, 439), in the form of a colourless oil.

TLC $SiO_2$ ($CH_2Cl_2$/MeOH/$NH_4OH$ 95/4.5/0.5) Rf=0.46; MS-ESI (m/z) 1058.5 (M+). Debenzylation according to the same process as in Example 20 provides the tetrahydro chloride. Melting point=209° C. MS-ESI (m/z) 656.3 (MH+).

EXAMPLE 27

Preparation of 2-{3-[4-(3-aminopropylamino)buty-lamino]propylamino}-N-[9-(4-hydroxy-3,5-dimethoxyphenyl)-8-oxo-5,5a,6,8,8a,9-hexahydro-furo[3',4':6,7]naphtho[2,3-d][1,3]dioxol-5-yl] acetamide This compound is obtained in 2 stages according to the process of Example 22 from the compound obtained according to Example 4 with benzyl{4-[(3-aminopropyl)-benzyloxycarbonylamino]butyl}(3-benzyloxycarbonylaminopropyl)carbamate (*Tet. Lett.*, 1998, 39, 439). The corresponding benzyl (3-benzyloxycarbonylaminopropyl)(4-{benzyloxycarbonyl-[3-({[9-(4-hydroxy-3,5-dimethoxyphenyl)-8-oxo-5,5a, 6,8,8a,9-hexahydrofuro[3',4':6,7]naphtho[2,3-d]dioxol-5-ylcarbamoyl]methyl}-amino)propyl]amino}butyl) carbamate intermediate is obtained (TLC $SiO_2$ $CH_2Cl_2$/MeOH/$NH_4OH$ 95/4.5/0.5); Rf=0.27. In a 2nd stage, debenzylation subsequently provides the tetrahydrochloride. Melting point=267° C. MS-ESI (m/z) 64.2 (MH+). Analysed: $C_{33}H_{47}N_5O_8$.4HCl; calculated: C %, 50.32; H %, 6.53; N %, 8.89. found: C %, 50.264; H %, 6.57; N %, 8.66.

EXAMPLE 28

Preparation of 2-{3-[4-(3-aminopropylamino)buty-lamino]propylamino}-N-[9-(3,4-dihydroxy-5-methoxyphenyl)-8-oxo-5,5aS,6,8,8a,9-hexahydrofuro[3',4':6,7]naphtho[2,3-d][1,3]dioxol-5-yl]acetamide This compound is obtained in 2 stages according to the process of Example 22 from the compound obtained in Example 5, 2-chloro-N-[9-(3,4-dihydroxy-5-methoxyphenyl)-8-oxo-5,5a,6,8,8a,9-hexahydrofuro[3',4':6,7]naphtho[2,3-d][1,3]dioxol-5-yl]acetamide, with benzyl{4-[(3-aminopropyl)benzyloxycarbonylamino]butyl}-(3-benzyloxycarbonylaminopropyl)carbamate (*Tet. Lett.*, 1998, 39, 439). The benzyl (3-benzyloxycarbonylaminopropyl)(4-{benzyloxycarbonyl-[3-({[9-(3,4-dihydroxy-5-methoxyphenyl)-8-oxo-5,5a,6,8,8a,9-hexahydrofuro[3',4':6,7]naphtho[2,3-d]dioxol-5-ylcarbamoyl]methyl}amino)propyl] amino}butyl)carbamate intermediate is obtained. TLC $SiO_2$ ($CH_2Cl_2$/MeOH/$NH_4OH$ 95/4.5/0.5); Rf=0.15. In a 2nd stage, 20 mg of 10% palladium-on-charcoal are added, after purging with nitrogen, to a solution of 90 mg of this intermediate in 10 ml of MeOH. Purging is carried out with a balloon swollen with hydrogen and the hydrogen atmosphere is maintained over the reaction medium with vigorous stifling for 1 hour. After purging with nitrogen, 0.1 ml of isopropanolic HCl solution (3.6N) is added to the medium, the catalyst is filtered off and rinsed with MeOH, and then the filtrate is evaporated to dryness. The residue is taken up in 20 ml of ethyl ether and the hydrochloride precipitate is filtered off and then dried. 20 mg of crystals are obtained (Yield 30%).

EXAMPLE 29

Preparation of 2-{3-[4-(3-aminopropylamino)-buty-lamino]propylamino}-N-[8-oxo-9-(3,4,5-trihydroxyphenyl)-5,5a,6,8,8a,9-hexahydrofuro[3',4':6,7]naphtho[2,3-d][1,3]dioxol-5-yl]acetamide This compound is obtained in 2 stages according to the process of Example 22 from the compound obtained in Example 7, 2-chloro-N-[9-(3,4,5-trihydroxyphenyl)-8-oxo-5,5a,6,8,8a,9-hexahydrofuro[3',4':6,7]naphtho[2,3-d][1,3] dioxol-5-yl]acetamide, with benzyl{4-[(3-aminopropyl)benzyloxycarbonylamino]butyl}(3-benzyloxycarbonylaminopropyl)carbamate (*Tet. Lett.*, 1998, 39, 439). The benzyl (3-benzyloxycarbonylaminopropyl)(4-{benzyloxycarbonyl-[3-({[(8-oxo-9(3,4,5-trihydroxyphenyl)-5,5a,6,8,8a,9-hexahydrofuro[3',4':6,7]naphtho[2,3-d]dioxol-5-ylcarbamoyl]methyl}amino)propyl]amino}butyl) carbamate intermediate is obtained. TLC $SiO_2$ ($CH_2Cl_2$/MeOH/$NH_4OH$ 95/4.5/0.5); Rf=0.15. In the 2nd stage, this intermediate is hydrogenolyzed according to the process of Example 28. A tetrahydrochloride is then obtained by precipitation from ethyl ether. Melting point=115° C.; MS-ESI (m/z) 613.3 (MH+).

EXAMPLE 30

Preparation of 2-(4-aminobutylamino)-N-[9-(3,4-dihydroxy-5-methoxyphenyl)-8-oxo-5,5a,6,8,8a,9-hexahydrofuro[3',4':6,7]naphtho[2,3-d][1,3]dioxol-5-yl]acetamide The intermediate possessing an N-benzyloxycarbonyl protective group is obtained by the same reaction sequence as in Example 25 but using the intermediate obtained in Example 5 instead of the intermediate obtained in Example 4; TLC $SiO_2$ ($CH_2Cl_2$/MeOH/$NH_4OH$ 90/9/1); Rf=0.26. Debenzylation according to the same process as in the second stage of Example 28 provides the dihydrochloride in the form of a cream powder. Melting point=94° C. This same compound is also obtained by the reaction of carbonic acid benzyl ester 2-benzyloxycarbonyloxy-5-[9-(2-chloroacetylamino)-6-oxo-5,5a,6,8,8a,9-hexahydrofuro[3',4':6,7]naphtho[2,3-d][1,3]dioxol-5-yl]-3-methoxyphenyl ester, itself obtained in Example 6, according to the procedure of Example 25, also using benzyl 4-aminobutylcarbamate, followed by hydrogenolysis.

EXAMPLE 31

Preparation of 2-[3-(3-aminobutylamino)propy-lamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is obtained in 2 stages according to the process of Example 22 from the compound obtained in Example 4 with benzyl{4-[(3-aminopropyl)benzyloxycarbonylamino]butyl}carbamate (*Synthesis*, 1994, 37). The corresponding benzyl (4-{benzyloxycarbonyl-[3-({[9-(4-hydroxy-3,5-dimethoxyphenyl)-8-oxo-5,5a,6,8,8a,9-hexahydrofuro[3',4':6,7]naphtho[2,3-d][1,3]dioxol-5-ylcarbamoyl]methyl}amino)propyl]amino}butyl)carbamate intermediate is obtained. In a 2nd stage, debenzylation according to the same process as in Example 22 provides the trihydrochloride. Melting point=255° C.; MS-ESI (m/z) 585.2 (MH+).

EXAMPLE 32

Preparation of 2-[4-(3-aminopropylamino)buty-lamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is obtained in 2 stages according to the process of Example 22 from the compound obtained in Example 4 with benzyl{3-(4-aminobutyl)benzyl-oxycarbonylamino]propyl}carbamate (*J. Org. Chem.*, 1998, 63, 9723). The corresponding benzyl(3-benzyloxycarbonylaminopropyl)-[4-({[9-(4-hydroxy-3,5-dimethoxyphenyl)-8-oxo-5,5a,6,8,8a,9-hexahydrofuro[3',4':6,7]naphtho[2,3-d][1,3]dioxol-5-ylcarbamoyl]methyl}amino)butyl]carbamate intermediate is obtained. In a 2nd stage, the benzylation according to the same process as in Example 22 provides the trihydrochloride. Melting point=199° C.; MS-ESI (m/z) 585.2 (M+); Analysed: $C_{30}H_{40}N_4O_8 \cdot 3HCl$; calculated: C %, 51.92; H %, 6.24; N %, 8.07. found: C %, 52.30; H %, 6.27; N %, 7.88.

EXAMPLE 33

Preparation of 2-[3-(3-aminopropylamino)propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is obtained in 2 stages according to the process of Example 22 from the compound obtained in Example 4 with benzyl (3-aminopropyl)(3-benzyloxycarbonylaminopropyl)carbamate (*Tet. Lett.*, 1994, 35, 2057 and 2061). The corresponding benzyl (3-benzyloxycarbonylaminopropyl)-[3-({[9-(4-hydroxy-3,5-dimethoxyphenyl)-8-oxo-5,5a,6,8,8a,9-hexahydrofuro[3',4':6,7]naphtho[2,3-d][1,3]dioxol-5-ylcarbamoyl]methyl}amino)propyl]carbamate intermediate is obtained. In a 2nd stage, debenzylation according to the same process as in Example 22 provides the trihydrochloride. MS-ESI (m/z) 571.2 (M+).

EXAMPLE 34

Preparation of 2-{3-[3-(3-aminopropylamino)propylamino]propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is obtained in 2 stages according to the process of Example 22 from the compound obtained in Example 4 with benzyl (3-aminopropyl){3-[benzyloxycarbonyl(3-benzyloxycarbonylaminopropyl)amino]propyl}carbamate prepared in an analogous way to the method of Example 27. In a 2nd stage, debenzylation according to the same process as in Example 22 provides 2-{3-[3-(3-aminopropylamino)propylamino]propylamino-}N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide tetrahydrochloride.
MS-ESI (m/z) 628.1 (M+).

EXAMPLE 35

Preparation of 2-{4-[4-(4-Aminobutylamino)butylamino]-butylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is obtained in 2 stages according to the process of Example 22 from the compound obtained in Example 4 with (4-aminobutyl){4-[benzyloxycarbonyl(4-benzyloxycarbonylaminobutyl)amino]butyl}carbamic acid benzyl ester, prepared in an analogous way to the method (*Synthesis*, 1994, 37). In a 2nd stage, after chromatographic purification, debenzylation according to the same process as in Example 22 provides 2-{4-[4-(4-aminobutylamino)butylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide tetrahydrochloride.
Melting point=263° C.; MS-ESI (m/z) 670.6 (M+).

EXAMPLE 36

Preparation of 2-[4-(4-Aminobutylamino)butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is obtained in 2 stages according to the process of Example 22 from the compound obtained in Example 4 with (4-aminobutyl)(4-benzyloxycarbonylaminobutyl)carbamic acid benzyl ester, prepared in an analogous way to the method (*Synthesis*, 1994, 37). In a 2nd stage, after chromatographic purification, debenzylation according to the same process as in Example 22 provides 2-[4-(4-aminobutylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide trihydrochloride.
Melting point=225° C.; MS-ESI (m/z) 600.2 (M+).

EXAMPLE 37

Preparation of 2-(5-Aminopentylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide This compound is obtained in 2 stages according to the process of Example 22 from the compound obtained in Example 4 with 5-(benzyloxycarbonylamino)penytlamine. In a 2nd stage, after chromatographic purification, debenzylation according to the same process as in Example 22 provides 2-(5-aminopentylamino)-N-[9-(4-dihydroxy-3,5-methoxyphenyl)-8-oxo-5,5a,6,8,8a,9-hexahydrofuro[3',4':6,7]naphtho[2,3-d][1,3]dioxol-5-yl]acetamide dihydrochloride.
Melting point=215° C.; MS-ESI (m/z) 543.1 (M+).

Pharmacological Results of the Compounds of the Invention

In vitro and in vivo Tests

1) In vitro Activity:

a) Cytotoxicity Test

The test used is the inhibition of growth of cells of the A549 human line (non-small-cell lung cancer):

The A549 tumour cells are seeded in a 96-well plate in RPMI 1640 medium without phenol red (Seromed) to which 5% of foetal calf serum is added (100 μl/well, $1.25 \times 10^4$ cell/ml). After incubating at 37° C. for 24 hours in an incubator comprising 5% $CO_2$, the medium is replaced with that comprising the test compound, after which the plates are incubated for an additional 48 hours. Cell survival is evaluated by measuring the luminescence after release of ATP into the medium using the cell lysis, luciferase and luciferin solutions present in the ATP-Lite-M™ kit as is recommended by the manufacturer (Packard, Rungis, France). Each experimental condition was tested at least three times as six identical copies. The results, expressed as $IC_{50}$ (M), are collated in Table I and show the cytotoxicity of the compounds.

b) Test for Detection of Breakages of the DNA in Cellulo:

The comets test is used. The breakages of the DNA are detected in the A549 cells after incubating for 1 hour with 10

µM of each of the test compounds. Etoposide and vinorelbine are used as positive and negative control respectively. The breakages are revealed using the comets test (*Br. J. Cancer,* 2000, 83, 1740). For each compound, twenty-five cells are analysed and the mean Tail Moment (TM) is calculated using Komet software (Kinetic Imaging, UK). The results are expressed with respect to the TM of etoposide, taken to be unity, and are collated in Table I. The advantage of the products of the present invention on the induction of their cleavage of the DNA, which is superior to that of etoposide, is thus shown.

TABLE I

In vitro activity

| Compound | Cytotoxicity, A549 cells, $IC_{50}$ (M) | TM |
|---|---|---|
| Etoposide | $1.8 \times 10^6$ | 1 |
| Vinorelbine | $3.7 \times 10^{-9}$ | 0 |
| Example 9 | $6 \times 10^{-6}$ | 2.81 |
| Example 12 | $2 \times 10^{-7}$ | 2.32 |
| Example 22 | $1 \times 10^{-6}$ | 3.89 |
| Example 25 | $8 \times 10^{-8}$ | 1.09 |
| Example 27 | $2 \times 10^{-7}$ | 1.22 |

2) In vivo Activity:

The compounds of the present invention have a solubility in water which makes possible a form of administration by infusion, by injection or by the oral route. They are provided in the form of their water-soluble hydrochloride, the solubility values of which are collated in Table II.

P388 experimental tumour model. The model used is P388 murine leukaemia (*Tumor Models in Cancer Research*, Teicher, B. A. ed., Humana Press Inc., Totowa, N.J., pp. 23-40, 2002), which is maintained by successive intraperitoneal transplantations in DBA/2 mice (DBA/2JIco, Charles River), as was described in prior art documents (Classic in vivo cancer models: Three examples of mouse models used in experimental therapeutics. *Current Protocols in Pharmacology Unit* 5.24: 5.24.1-5.24.16, 2001).

The experiment is carried out according to a protocol already described in prior art documents (*Cancer Chemother. Pharmacol.*, 1998, 41, 437-447). This consists in implanting $10^6$ cells of P388 leukaemia per mouse into C2DF1 hybrid mice (CD2F1/Cr1BR, Charles River, St Aubin-les-Elbeuf, France) intravenously on day zero. After randomizing the animals in the treatment and control cages, the compounds to be evaluated are administered in a single injection intraperitoneally the day after the tumour graft, on day 1. The animals are subsequently monitored every day, weighed twice weekly and any clinical reaction is recorded. The survival is the parameter for evaluation of the antitumour activity. The increase in survival is defined by the T/C$_{survival}$ ratio (%), corresponding to: (Median of survival of the treated group/Median of survival of the control group)×100. A T/C$_{survival}$ ratio is calculated for each dose administered and the greatest value obtained represents the maximum increase in survival achieved (maximum activity), which is defined by the optimum T/C$_{survival}$ ratio. The results are illustrated in Table II, in which the optimum T/C$_{survival}$ values appear. The results show that the compounds of Examples 9, 12, 25 and 27 have resulted in a significant increase in survival of the animals carrying P388 leukaemia, which is reflected by optimum T/C$_{survival}$ values of 129 to 157%, indicating that the treatment of the animals with these compounds has made it possible to prolong the survival of the animals by 29 to 57%. Specifically, according to the criteria of the NCI (National Cancer Institute), a T/C$_{survival}$ value is regarded as significant if it is at least greater than 120% (*Semin. Oncol.*, 1981, 8, 349-361).

The relative loss in body weight of the animals, associated with the optimum activity of the compounds, is much less than the toxicity threshold, according to the criteria of the NCI (*Ann. Oncol.*, 1994, 5, 415-422).

B16 experimental tumour model. The model used is the B16 melanoma (*Tumor Models in Cancer Research*, Teicher, B. A. ed., Humana Press Inc., Totowa, N.J., pp. 23-40, 2002), which is maintained by successive subcutaneous transplantations in C57BL/6 mice (C57BL/6 NCr1BR, Charles River, St Aubin-les-Elbeuf, France), as was described above (Classic in vivo cancer models: Three examples of mouse models used in experimental therapeutics. *Current Protocols in Pharmacology Unit* 5.24: 5.24.1-5.24.16, 2001).

The experiment is carried out according to a protocol already described above. B16 tumour tissue is ground and homogenized in a 0.9% sterile sodium chloride solution using a Dounce homogenizer and then C57BL/6 mice are inoculated subcutaneously into the flank with 0.5 ml of this 1 g/ml preparation on day zero. After randomizing the animals in the treatment and control cages, the compounds to be evaluated are administered intraperitoneally on days 3, 5, 7 and 10 after the grafting of the tumour. The animals are subsequently monitored every day, weighed twice weekly and any clinical reaction is recorded. The size of the tumour is measured three times weekly during the experiment. The tumour volume is calculated and the activity of the compounds on the size of the tumour is defined by the T/C$_{volume}$ ratio (%), corresponding to (Median tumour volume of the treated group/Median tumour volume of the control group)×100.

The results are illustrated in Table II, in which the optimum T/C$_{volume}$ values appear. The results show, inter alia, that the compounds of Examples 25 and 27 result in a significant slowing in the tumour growth, which is respectively reflected by optimum T/C$_{volume}$ values of 25% and 7%. Specifically, according to the criteria of the NCI (National Cancer Institute), a T/C$_{volume}$ value is regarded as significant if it is at least less than 42% (*Cancer Res.*, 1991, 51, 4845-4852).

TABLE II

In vivo antitumour activity

| Compound | Solubility in water (mg/ml) | P388 Model Optimum T/C$_{survival}$ (%) [dose, mg/kg] | B16 Model Optimum T/C$_{volume}$ (%) [dose, mg/kg] | MX-1 Model Optimum T/C$_{volume}$ (%) [dose, mg/kg] |
|---|---|---|---|---|
| Example 9 | 100 | 157 [10] | — | — |
| Example 12 | 16 | 157 [2.5] | — | — |
| Example 25 | 100 | 129 [10] | 25 [20] | 51 [10] |
| Example 27 | 50 | 129 [7.5] | 7 [7.5] | 0 [2.5] |

MX-1 experimental tumour model. The model used is a human mammary carcinoma (Developmental Therapeutics Program, Division of Cancer Treatment, National Cancer Institute, In vivo Cancer Models 1976-1982. NIH Publication No. 84 2635, Washington D.C.: United States Government Printing Office, 1984), which is maintained by successive subcutaneous transplantations in Swiss Nude mice (Ico: Swiss-nu/nu, Iffa Credo, L'Arbresle, France), as was described above (Classic in vivo cancer models: Three examples of mouse models used in experimental therapeutics. *Current Protocols in Pharmacology Unit* 5.24: 5.24.1-5.24.16, 2001).

The experiment is carried out according to a protocol already described above (*Cancer Chemother. Pharmacol.*, 1998, 41, 437-447). Swiss Nude mice are grafted subcutaneously into the flank with a fragment of MX-1 tumour on day zero. After randomizing the animals in their treatment and control cages, the compounds to be evaluated are administered intraperitoneally on day 7, 9, 11, 14, 16 and 18 after the grafting of the tumour. The animals are subsequently monitored every day, weighed twice weekly and any clinical reaction is recorded. The size of the tumour is measured three times weekly during the experiment. The tumour volume is calculated and the activity of the compounds on the size of the tumour is defined by the $T/C_{volume}$ ratio (%), corresponding to (Median tumour volume of the treated group/Median tumour volume of the control group)×100. The results are collated in Table II. The compound of Example 25 exhibits a $T/C_{volume}$ ratio (%) of 51% for a treatment of 10 mg/kg and the compound of Example 27 exhibits a $T/C_{volume}$ ratio (%) of 0% for a treatment of 2.5 mg/kg, thus showing complete eradication of the tumour.

The invention claimed is:

1. Compounds of general formula (I)

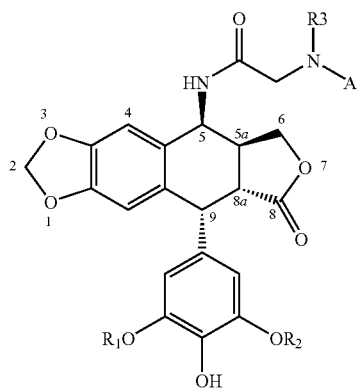

in which
R$_1$ and R$_2$ are selected from the group consisting of a hydrogen atom and a methyl radical;
R3 and A together form a C$_3$-C$_8$ saturated aliphatic ring, comprising one or more heteroatoms or
R3 represents a radical chosen from the group consisting of a hydrogen atom, a C$_1$-C$_4$ alkyl radical and a benzyl radical and A represents a radical chosen from the group consisting of a hydrogen atom, a C$_1$-C$_4$ alkyl radical, a benzyl radical and a group of formula (II)

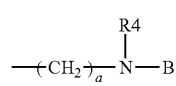

in which a varies from 2 to 5,
R4 and B together form a C$_3$-C$_8$ ring
or
R4 represents a radical chosen from the group consisting of a hydrogen atom, a C$_1$-C$_4$ alkyl radical and a benzyl radical, it being possible for R3 and R4 to be connected by an alkylene chain comprising 2 or 3 carbon atoms, and B represents a radical chosen from the group consisting of:
a hydrogen atom,
a C$_1$-C$_4$ alkyl radical,
a benzyl radical,
a group of formula (III)

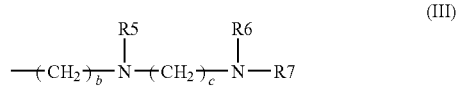

in which b varies from 2 to 5 and c varies, from 2 to 5 and R5 to R7 are a radical chosen from the group consisting of a hydrogen atom, a C$_1$-C$_4$ alkyl radical and a benzyl radical, it being possible for R4 and R5 and/or R5 and R6 and/or R6 and R7 to be connected by an alkylene chain comprising 2 or 3 carbon atoms;
and a group of formula (IV)

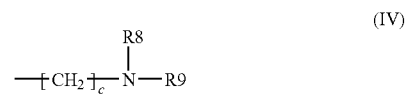

in which c varies from 2 to 5 and R8 and R9 represent, each independently of one another, a hydrogen atom or a C$_1$-C$_5$ alkyl radical, it being possible for R4 and R8 to be connected by an alkylene chain comprising 2 or 3 carbon atoms, or R8 and R9 together form a C$_3$-C$_8$ ring; or their pharmaceutically acceptable salts, in particular their addition salts, with inorganic or organic acids.

2. Compounds according to claim 1, wherein R3 to R9 represent, independently of one another, a hydrogen atom or a C$_1$-C$_4$ alkyl radical.

3. Compounds according to claim 1, wherein R3 represents a hydrogen atom or a methyl radical and A represents a hydrogen atom, a methyl radical or a group of formula (II) in which R4 represents a hydrogen atom, a methyl radical or an ethyl radical and B represents a radical chosen from the group consisting of:
a hydrogen atom,
a methyl radical,
an ethyl radical,
a group of formula (III) in which R5, R6 and R7 represent a hydrogen atom, a C$_1$-C$_4$ alkyl radical or a benzyl radical,
a group of formula (IV) in which R8 and R9, which are identical, represent a hydrogen atom or a methyl radical.

4. Compounds according to claim 1, wherein they are chosen from the group consisting of:
2-(2-dimethylaminoethylamino)-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-2-(2-(morpholin-4-yl)ethylamino)-acetamide
2-[(2-dimethylaminoethyl)methylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide
2-dimethylamino-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]acetamide N-[9-(4-hydroxy-3,5-dimethoxyphenyl)-8-oxo-5,5a,6,8,
8a,9-hexahydrofuro[3',4':6,7]naphtho[2,3-d][1,3]di-
oxol-5-yl]-2-(piperidin-1-yl)acetamide 2-benzylamino-N-[9-(4-hydroxy-3,5-dimethoxyphenyl)-
8-oxo-5,5a,6,8,8a,9-hexahydrofuro[3',4':6,7]naphtho
[2,3-d][1,3]dioxol-5-yl]acetamide N-[9-(4-hydroxy-3,5-dimethoxyphenyl)-8-oxo-5,5a,6,8,
8a,9-hexahydrofuro[3',4':6,7]naphtho[2,3-d][1,3]di-
oxol-5-yl]-2-(piperazin-1-yl)acetamide 2-(4-benzylpiperazin-1-yl)-N-[9-(4-hydroxy-3,5-
dimethoxyphenyl)-8-oxo-5,5a,6,8,8a,9-hexahydrofuro
[3',4':6,7]naphtho[2,3-d][1,3]dioxol-5-yl]acetamide 2-ethylamino-N-[9-(4-hydroxy-3,5-dimethoxyphenyl)-8-
oxo-5,5a,6,8,8a,9-hexahydrofuro[3',4':6,7]naphtho[2,
3-d][1,3]dioxol-5-yl]acetamide N-[9-(4-hydroxy-3,5-dimethoxyphenyl)-8-oxo-5,5a,6,8,
8a,9-hexahydrofuro[3',4':6,7]naphtho[2,3-d][1,3]di-
oxol-5-yl]-2-(propylamino)acetamide 2-butylamino-N-[9-(4-hydroxy-3,5-dimethoxyphenyl)-8-
oxo-5,5a,6,8,8a,9-hexahydrofuro[3',4':6,7]naphtho[2,
3-d][1,3]dioxol-5-yl]acetamide 2-(2-diethylaminoethylamino)-N-[9-(4-hydroxy-3,5-
dimethoxyphenyl)-8-oxo-5,5a,6,8,8a,9-hexahydrofuro
[3',4':6,7]naphtho[2,3-d][1,3]dioxol-5-yl]acetamide 2-(2-diethylaminopropylamino)-N-[9-(4-hydroxy-3,5-
dimethoxyphenyl)-8-oxo-5,5a,6,8,8a,9-hexahydrofuro
[3',4':6,7]naphtho[2,3-d][1,3]dioxol-5-yl]acetamide 2-amino-N-[9-(4-hydroxy-3,5-dimethoxyphenyl)-8-oxo-
5,5a,6,8,8a,9-hexahydrofuro[3',4':6,7]naphtho[2,3-d]
[1,3]dioxol-5-yl]acetamide 2-(2-aminoethylamino)-N-[9-(4-hydroxy-3,5-dimethox-
yphenyl)-8-oxo-5,5a,6,8,8a,9-hexahydrofuro[3',4':6,7]
naphtho[2,3-d][1,3]dioxol-5-yl]acetamide 2-(3-aminopropylamino)-N-[9-(4-hydroxy-3,5-
dimethoxyphenyl)-8-oxo-5,5a,6,8,8a,9-hexahydrofuro
[3',4':6,7]naphtho[2,3-d][1,3]dioxol-5-yl]acetamide 2-(4-aminobutylamino)-N-[9-(4-hydroxy-3,5-dimethox-
yphenyl)-8-oxo-5,5a,6,8,8a,9-hexahydrofuro[3',4':6,7]
naphtho[2,3-d][1,3]dioxol-5-yl]acetamide 2-{3-[4-(3-aminopropylamino)butylamino]propy-
lamino}-N-[9-(4-hydroxy-3,5-dimethoxyphenyl)-8-
oxo-5,5a,6,8,8a,9-hexahydrofuro[3',4':6,7]naphtho[2,
3-d][1,3]dioxol-5-yl]acetamide 2-{3-[4-(3-aminopropylamino)butylamino]propy-
lamino}-N-[9-(3,4-dihydroxy-5-methoxyphenyl)-8-
oxo-5,5aS,6,8a,9-hexahydrofuro[3',4':6,7]naphtho[2,3-
d][1,3]dioxol-5-yl]acetamide 2-{3-[4-(3-aminopropylamino)butylamino]propy-
lamino}-N-[8-oxo-9-(3,4,5-trihydroxyphenyl)-5,5a,6,
8,8a,9-hexahydrofuro[3',4':6,7]naphtho[2,3-d][1,3]di-
oxol-5-yl]acetamide 2-(4-aminobutylamino)-N-[9-(3,4-dihydroxy-5-methox-
yphenyl)-8-oxo-5,5a,6,8,8a,9-hexahydrofuro[3',4':6,7]
naphtho[2,3-d][1,3]dioxol-5-yl]acetamide 2-[3-(4-aminobutylamino)propylamino]-N-[9-(4-hy-
droxy-3,5-dimethoxyphenyl)-8-oxo-5,5a,6,8,8a,9-
hexahydrofuro[3',4':6,7]naphtho[2,3-d][1,3]dioxol-5-
yl]acetamide 2-[4-(3-aminopropylamino)butylamino]-N-[9-(4-hy-
droxy-3,5-dimethoxyphenyl)-8-oxo-5,5a,6,8,8a,9-
hexahydrofuro[3',4':6,7]naphtho[2,3-d][1,3]dioxol-5-
yl]acetamide 2-[3-(3-aminopropylamino)propylamino]-N-[9-(4-hy-
droxy-3,5-dimethoxyphenyl)-8-oxo-5,5a,6,8,8a,9-
hexahydrofuro[3',4':6,7]naphtho[2,3-d][1,3]dioxol-5-
yl]acetamide 2-[4-(4-aminobutylamino)butylamino]-N-[9-(4-hydroxy-
3,5-dimethoxyphenyl)-8-oxo-5,5a,6,8,8a,9-hexahydro-
furo[3',4':6,7]naphtho[2,3-d][1,3]dioxol-5-yl]aceta-
mide 2-{3-[3-(3-aminopropylamino)propylamino]propy-
lamino}-N-[9-(4-hydroxy-3,5-dimethoxyphenyl)-8-
oxo-5,5a,6,8,8a,9-hexahydrofuro[3',4':6,7]naphtho[2,
3-d][1,3]dioxol-5-yl]acetamide 2-{4-[4-(4-aminobutylamino)butylamino]butylamino}-
N-[9-(4-hydroxy-3,5-dimethoxyphenyl)-3-oxo-5,5a,6,
8,8a,9-hexahydrofuro[3',4':6,7]naphtho[2,3-d][1,3]di-
oxol-5-yl]acetamide 2-[4-(4-aminobutylamino)butylamino]-N-[9-(4-hydroxy-
3,5-dimethoxyphenyl)-8-oxo-5,5a,6,8,8a,9-hexahydro-
furo[3',4':6,7]naphtho[2,3-d][1,3]dioxol-5-yl]aceta-
mide 2-(5-aminopentylamino)-N-[9-(4-hydroxy-3,5-dimethox-
yphenyl)-8-oxo-5,5a,6,8,8a,9-hexahydrofuro[3',4':6,7]
naphtho[2,3-d][1,3]dioxol-5-yl]acetamide and/or their addition salts with inorganic or organic acids.

5. Pharmaceutical composition, comprising at least one compound of formula (I) according to claim 1 and an excipient for administration by oral or parenteral route.

6. A compound according to claim 1, which is:
(2-{3-[4-(3-aminopropylamino)-butylamino]-propy-
lamino}-N-[9-(4-hydroxy-3,5-dimethoxyphenyl)-8-
oxo-5,5,6,8,8a,9-hexahydrofuro[3',4':6,7]naptho[2,3-d]
[1,3]dioxol-5-yl]-acetamide, or a pharmaceutically acceptable salt thereof.

7. The compound of claim 6, wherein the pharmaceutically acceptable salt thereof is hydrochloric acid.

8. A compound which is:
(2-{3-[4-(3-aminopropylamino)-butylamino]-propy-
lamino}-N-[9-(4-hydroxy-3,5-dimethoxyphenyl)-8-
oxo-5,5,6,8,8a,9-hexahydrofuro[3',4':6,7]naptho[2,3-d]
[1,3]dioxol-5-yl]-acetamide tetrahydrochloric acid.

* * * * *